United States Patent [19]

Massie

[11] 3,985,796

[45] Oct. 12, 1976

[54] HYDROXYLATION OF AROMATIC COMPOUNDS

[75] Inventor: Stephen N. Massie, Palatine, Ill.

[73] Assignee: UOP Inc., Des Plaines, Ill.

[22] Filed: Oct. 1, 1975

[21] Appl. No.: 618,540

Related U.S. Application Data

[63] Continuation-in-part of Ser. No. 491,008, July 23, 1974, Pat. No. 3,931,295.

[52] U.S. Cl.................... 260/502.4 R; 260/502.4 P; 260/502.5; 260/509; 260/510; 260/512 R; 260/512 C; 260/519; 260/520 E; 260/521 B; 260/521 P; 260/521 H; 260/521 N; 260/523 R; 260/523 A; 260/621 G; 260/520 R

[51] Int. Cl.²................... C07F 9/38; C07F 143/64; C07F 143/44; C07C 65/04

[58] Field of Search............. 260/621 G, 502.4 R, 260/502.4 P, 502.5, 509, 510, 512 R, 512 C, 519, 520, 521 B, 521 P, 521 H, 521 N, 523 R, 523 A

[56] References Cited
UNITED STATES PATENTS

| | | | |
|---|---|---|---|
| 2,395,638 | 2/1946 | Milas | 260/621 G |
| 2,437,648 | 3/1948 | Milas | 260/621 G |
| 3,531,519 | 9/1970 | Parkin et al. | 260/621 G |
| 3,580,956 | 5/1971 | Bloch | 260/621 G |
| 3,600,446 | 8/1971 | Massie | 260/621 G |

*Primary Examiner*—Joseph E. Evans
*Attorney, Agent, or Firm*—James R. Hoatson, Jr.; Raymond H. Nelson; William H. Page, II

[57] ABSTRACT

The nuclear hydroxylation of aromatic compounds is effected by treating said compounds with hydrogen peroxide in the presence of a catalyst comprising an alkaline solution containing an aliphatic nitrile compound at conditions which include a temperature in the range of from $-10°$ to about $100°$ C. and a pressure in the range of from about atmospheric to about 100 atmospheres.

9 Claims, No Drawings

HYDROXYLATION OF AROMATIC COMPOUNDS

CROSS-REFERENCE TO RELATED APPLICATION

This application is a continuation-in-part of my copending application Ser. No. 491,008 filed July 23, 1974, now U.S. Pat. No. 3,931,295, all teachings of which are incorporated herein by reference thereto.

This invention relates to a process for the nuclear hydroxylation of aromatic compounds. More particularly, this invention relates to a process for the nuclear hydroxylation of aromatic compounds having the formula $R_mArX_nH$ in which Ar is a monocyclic or polycyclic hydrocarbon nucleus, R is selected from the group consisting of carboxylic, sulfonic or phosphonic acid radicals, the alkali metal salts or alkaline earth metal salts of the acid radical, X is independently selected from the group consisting of hydrogen, alkyl, aryl, cycloalkyl, alkoxy, halogen, hydroxy and amino substituents, $m$ being an integer from 1 to about 5 and $n$ being an integer between 0 and 5, the sum of $m$ and $n$ being 5, which comprises treatment of said aromatic compounds with hydrogen peroxide in the presence of a catalyst comprising an alkaline solution containing an aliphatic organic nitrile compound.

Hydroxylated aromatic acids are finding a wide variety of uses in the chemical field. For example, α-resorcylic acid which is also known as 3,5-dihydroxybenzoic acid is used as an intermediate for dyes, pharmaceuticals, light stabilizers and resins; β-resorcylic acid which is also known as 2,4-dihydroxybenzoic acid is also used as a dye stuff, as an intermediate in the preparation of pharmaceuticals or in the synthesis of organic chemicals. A third isomer of the dihydroxybenzoic acid which is gentisic acid also known as 2,5-dihydroxybenzoic acid is used in medicine as sodium gentissate. Another hydroxylated aromatic compound is gallic acid also known as 3,4,5-trihydroxybenzoic acid which is used for a variety of purposes including its use in photography, writing inks, dyeing, in the manufacturing of pyrogallol which itself has many uses, as a tanning agent and in the manufacture of tannins, in the manufacture of paper; in synthesis of pharmaceuticals, in process engraving, and lithography, etc. The hydroxylated benzenesulfonic acids and phosphonic acids may also be utilized in the synthesis of pharmaceuticals, paper manufacturing, as tanning agents and in process engraving. The hydroxylated aromatic acid will have similar utility as hereinbefore set forth for the hydroxylated aromatic acids.

It is therefore an object of this invention to provide a process for hydroxylating aromatic acids or their alkali or alkaline earth metal salts.

A further object of this invention is to provide a process for introducing hydroxy substituents on the nucleus of the various aromatic acids or their alkali or alkaline earth metal salts to provide a useful chemical compound.

In one aspect an embodiment of this invention resides in a process for the nuclear hydroxylation of an aromatic compound having the formula:

in which Ar is a monocyclic or polycyclic hydrocarbon nucleus, R is selected from the group consisting of carboxylic, sulfonic, phosphonic acid groups, alkali metal or alkaline earth metal salts of the acids, X is independently selected from the group consisting of hydrogen, alkyl, aryl, cycloalkyl, alkoxy, aralkyl, alkaryl, halogen, hydroxy and amino substituents, $m$ is an integer of from 1 to about 5 and $n$ is an integer of from 0 to 5, which comprises reacting said aromatic compound with hydrogen peroxide at hydroxylation conditions in the presence of a catalyst comprising an alkaline solution containing an aliphatic nitrile compound, and recovering the resultant hydroxylated aromatic compound.

A specific embodiment of this invention is found in a process for preparing 2-hydroxybenzenephosphonic acid which comprises treating benzenephosphonic acid with hydrogen peroxide at a temperature in the range of from about −10° to about 100° C., a pressure in the range of from about atmospheric to about 100 atmospheres, and a mole ratio of from about 1:1 to about 1:10 moles of hydrogen peroxide per mole of benzenephosphonic acid in the presence of a catalyst comprising propionitrile in an aqueous potassium hydroxide solution and recovering the resultant 2-hydroxybenzenephosphonic acid.

Other objects and embodiments will be found in the following further detailed description of the present invention.

As hereinbefore set forth the present invention is concerned with the process for preparing hydroxylated aromatic compounds, said process being effected by treating an aromatic compound with hydrogen peroxide in the presence of a catalyst comprising an alkaline solution containing an aliphatic organic nitrile compound. The reaction is effected under conditions which include a temperature in the range of from about −10° C. to about 150° C. and preferably from about 0° to about 100° C. In addition, another reaction condition involves pressure, said pressure ranging from about atmospheric up to 100 atmospheres or more. When superatmospheric pressures are employed, said pressure is afforded by the introduction of a substantially inert gas such as nitrogen or helium into the reaction zone. Another variable which may be employed in the present invention is the amount of reactants, the hydrogen peroxide usually being present in a mole ratio in the range of from about 1:1 up to 1:10 moles of the hydrogen peroxide per mole of the aromatic compound.

Aromatic compounds which comprise the starting material for the process of this invention possess the generic Formula I:

in which Ar is a monocyclic or polycyclic hydrocarbon nucleus, R is selected from the group consisting of carboxylic, sulfonic, or phosphonic acid radicals, the alkali metal salt or alkaline earth metal salts of the acid radicals, X is independently selected from the group consisting of hydrogen, alkyl, aryl, cycloalkyl, alkoxy, aralkyl, alkaryl, halogen, hydroxy and amino substituents, $m$ being an integer of from 1 to about 5 and $n$ being an integer between 0 and 5, the total of $m$ and $n$ equaling 5. Some specific examples of these aromatic compounds which undergo nuclear hydroxylation will include benzoic acid, benzenesulfonic acid, benzenephosphonic acid, p-toluic acid, o-toluic acid, m-toluic acid, o-methylbenzenesulfonic acid, p-methylbenzenesulfonic acid, o-ethylbenzenesulfonic acid, m-ethylbenzoic acid, p-ethylbenzenephosphonic acid, o-propylbenzoic acid, m-propylbenzenesulfonic acid, p-propylbenzenephosphonic acid, o-isopropylbenzoic acid, m-isopropylbenzenesulfonic acid, p-isopropylbenzenephosphonic acid, o-n-butylbenzoic acid, m-n-butylbenzenesulfonic acid, p-n-butylbenzenephosphonic acid, 2,4-dimethylbenzoic acid, 2,5-dimethylbenzenesulfonic acid, 2,6-dimethylbenzenephosphonic acid, 2,4-ethylbenzoic acid, 2,5-diethylbenzenesulfonic acid, 2,6-diethylbenzenephosphonic acid, 2,4-dipropylbenzenesulfonic acid, 2,5-dipropylbenzenesulfonic acid, 2,6-dipropylbenzenesulfonic acid, 2,4-diisopropylbenzenephosphonic acid, 2,5-diisopropylbenzenephosphonic acid, 2,6-diisopropylbenzoic acid, 2,4,6-trimethylbenzoic acid, o-cyclohexylbenzoic acid, m-cyclohexylbenzenesulfonic acid, p-cyclohexylbenzenephosphonic acid, o-phenylbenzoic acid, m-phenylbenzenesulfonic acid, p-phenylbenzenephosphonic acid, o-benzylbenzoic acid, o-[4-tolyl]benzoic acid, m-[4-tolyl]benzenesulfonic acid, p-[4-tolyl]benzenephosphonic acid, o-methoxybenzoic acid, m-methoxybenzenesulfonic acid, p-methoxybenzenephosphonic acid, o-ethoxybenzoic acid, m-ethoxybenzenesulfonic acid, p-ethoxybenzenephosphonic acid, 2,3,4,5-tetramethylbenzenesulfonic acid, 2,3,4,6-tetraethylbenzenephosphonic acid, 2-chlorobenzoic acid, 2-chlorobenzenesulfonic acid, 2-chlorobenzenephosphonic acid, 2,3-dichlorobenzoic acid, 2,3-dichlorobenzenesulfonic acid, 2,3-dichlorobenzenephosphonic acid, 2,3,4-trichlorobenzoic acid, 2,3,4-trichlorobenzenesulfonic acid, 2,3,4-trichlorobenzenephosphonic acid, 2-bromobenzoic acid, 2-bromobenzenesulfonic acid, 2-bromobenzenephosphonic acid, 2,3-dibromobenzoic acid, 2,3,4-tribromobenzenephosphonic acid, 2,3,4,5-tetrachlorobenzoic acid, 2,3,4,5-tetrabromobenzenesulfonic acid, 2,3,4,5-tetrabromobenzenephosphonic acid, 2-aminobenzenesulfonic acid, 2-aminobenzenephosphonic acid, 2-aminobenzoic acid, 2,3-diaminobenzoic acid, 2,3-diaminobenzenephosphonic acid, 2,3-diaminobenzenesulfonic acid, 2,3,4-triaminobenzoic acid, 2,3,4-triaminobenzenesulfonic acid, 2,3,4-triaminobenzenephosphonic acid, 2,3,4,5-tetraaminobenzenesulfonic acid, naphthoic acid, o-hydroxybenzoic acid, m-hydroxybenzoic acid, p-hydroxybenzoic acid, 2,4-dihydroxybenzoic acid, 3,5-dihydroxybenzoic acid, α-anthranoic acid, β-phenanthanoic acid, α-pyric acid, α-naphthalenesulfonic acid, β-naphthalenephosphonic acid, etc. It is also contemplated within the scope of this invention that the starting material may also comprise the alkali metal salt or the alkaline earth metal salts of the various carboxylic, sulfonic and phosphonic acids. Suitable examples of these salts would include sodium benzoate, sodium benzenesulfonate, sodium benzenephosphonate, lithium benzoate, lithium benzenesulfonate, lithium benzenephosphonate, potassium benzoate, potassium benzenesulfonate, potassium benzenephosphonate, rubidium benzoate, rubidium benzenesulfonate, rubidium benzenephosphonate, cesium benzoate, cesium benzenesulfonate, cesium benzenephosphonate, magnesium benzoate, magnesium benzenesulfonate, magnesium benzenephosphonate, calcium benzoate, calcium benzenesulfonate, calcium benzenephosphonate, strontium benzoate, strontium benzenesulfonate, strontium benzenephosphonate, barium benzoate, barium benzenesulfonate, barium benzenephosphonate, sodium terephthalate, calcium phthalate, calcium isophthalate, 2-methyl sodium benzoate, calcium benzenesulfonate, magnesium 3-methylbenzenephosphonate, cesium benzenesulfonate, rubidium 3-chlorobenzenephosphonate, sodium 2,3-dichlorobenzoate, rubidium 2-aminobenzenephosphonate, 2,4-diaminobenzenephosphonate, etc.

It is contemplated within the scope of this invention that the aromatic compound may be treated with hydrogen peroxide (formula = $H_2O_2$) at hydroxylation conditions in the presence of a catalyst comprising an alkaline solution containing an aliphatic organic nitrile compound. The term "alkaline solution" as used in the specification and the appended claims is defined to mean a solution in which there remains free base such as sodium hydroxide or potassium hydroxide present after any free carboxylic, sulfonic, phosphonic acid or hydroxyl groups are neutralized plus an equivalent amount of base for each mole of hydrogen peroxide charged. As hereinbefore set forth the alkaline solution contains an aliphatic organic nitrile compound. Suitable examples of aliphatic organic nitriles would include those containing from 2 to about 10 carbon atoms such as acetonitrile, propionitrile, butyronitrile, pentanonitrile, capronitrile, heptanonitrile, caprylnitrile, pelargonitrile, caprinitrile, etc. The alkaline solution of the catalyst of the present invention may be afforded by the presence of any relatively strong base such as sodium hydroxide, potassium hydroxide, calcium hydroxide, lithium hydroxide, magnesium hydroxide, etc. It is understood that the aforementioned aromatic compounds and catalysts comprising an alkaline solution containing an aliphatic organic nitrile compound are only representative of the class of compounds which may be used and that the present invention is not necessarily limited thereto.

The process of the present invention may be effected in either a batch or continuous type operation. For example, when a batch type operation is used, a quantity of the aromatic acid or acid salt is placed in an appropriate apparatus such as, for example, a stirred autoclave along with a catalyst comprising an alkaline solution containing an aliphatic organic nitrile compound. The hydrogen peroxide is added thereto and the reaction allowed to proceed for a predetermined residence time under the hydroxylation conditions hereinbefore set forth in greater detail. The residence time may vary from about 0.5 hour up to about 5 hours or more in duration depending on the temperature selected. Upon completion of the desired residence time, the reaction product is recovered. Following this, the reaction product is subjected to conventional means for recovery, said means including washing the product with an inert organic solvent, flashing off the solvent and subjecting the reaction product to fractional distillation or crystallization to recover the desired compounds.

It is also contemplated that the process of this invention may be effected in a continuous manner of operation. When such a process is used the aromatic compound which is to undergo hydroxylation and the catalyst comprising an alkaline solution containing an aliphatic organic nitrile compound are continuously charged to a reaction zone in which proper operating conditions of temperature and pressure are maintained. The alkalinity of the solution is maintained or modified by an on-stream pH meter. In addition, the hydrogen peroxide in the form of an aqueous solution containing from about 5% to about 90% or more of hydrogen peroxide is continuously charged to the reaction zone in slow and deliberate manner. The reaction is allowed to proceed for a predetermined residence time, following which the reactor effluent is continuously withdrawn. The reaction product in the reactor effluent is separated from the unreacted aromatic compound by conventional means of the type hereinbefore set forth and passed to storage while any unreacted aromatic compound or catalyst comprising an alkaline solution containing an aliphatic organic nitrile may be recycled to form a portion of the feed stock.

Examples of hydroxylated aromatic compounds which may be prepared according to the process of this invention include o-hydroxybenzoic acid, m-hydroxybenzoic acid, p-hydroxybenzoic acid, 5-hydroxy-o-toluic acid, 3,4-hydroxy-o-toluic acid, 5-hydroxy-m-toluic acid, 5-hydroxy-p-toluic acid, 3,5-dihydroxy-p-toluic acid, 5-hydroxy-2-ethylbenzoic acid, 5-hydroxy-3-ethylbenzenesulfonic acid, 5-hydroxy-3-ethylbenzenephosphonic acid, 3-hydroxy-4-ethylbenzoic acid, 3,4-dihydroxy-4-ethylbenzenesulfonic acid, 5-hydroxy-2-propylbenzenephosphonic acid, 5-hydroxy-3-propylbenzoic acid, 3-hydroxy-4-propylbenzenesulfonic acid, 3,5-dihydroxy-4-propylbenzenephosphonic acid, 5-hydroxy-2-isopropylbenzoic acid, 5-hydroxy-3-isopropylbenzenesulfonic acid, 3-hydroxy-4-isopropylbenzenephosphonic acid, 3,5-dihydroxy-4-isopropylbenzoic acid, 5-hydroxy-o-n-butylbenzenesulfonic acid, 5-hydroxy-3-n-butylbenzenephosphonic acid, 3-hydroxy-4-t-butylbenzoic acid, 3,5-dihydroxy-4-n-butylbenzenesulfonic acid, 3-hydroxy-4-n-butylbenzenephosphonic acid, 3,5-dihydroxy-4-n-butylbenzoic acid, 3-hydroxy-2,4-dimethylbenzesulfonic acid, 3-hydroxy-2,5-dimethylbenzenephosphonic acid, 5-hydroxy-2,6-dimethylbenzoic acid, 5-hydroxy-2,4,6-trimethylbenzenesulfonic acid, 3,5-dihydroxy-2,4,6-trimethylbenzenephosphonic acid, 5-hydroxy-2-cyclohexylbenzoic acid, 5-hydroxy-2-phenylbenzenesulfonic acid, 3,5-dihydroxy-4-phenylbenzenephosphonic acid, 2,3-dihydroxybenzoic acid, 3,4-dihydroxybenzenesulfonic acid, 2,5-dihydroxybenzenephosphonic acid, 3,4,5-trihydroxybenzoic acid, 2,3-dihydroxy-4-methylbenzenesulfonic acid, 2,5-dihydroxy-4-methylbenzenephosphonic acid, 5-hydroxy-2-methoxybenzenephosphonic acid, 5-hydroxy-2-methoxybenzoic acid, 3,5-dihydroxy-4-methoxybenzenesulfonic acid, 5-hydroxy-2-ethoxybenzenephosphonic acid, 3-hydroxy-4-ethoxybenzoic acid, 3,5-dihydroxy-4-ethoxybenzenesulfonic acid, 4-hydroxy-1-methyl-2-naphthoic acid, 3,4-dihydroxy-1-methyl-2-naphthoic acid, 1,4-dihydroxy-2-naphthoic acid, 3,4-dihydroxy-1-naphthoic acid. It is also contemplated within the hydroxylation of the aromatic compound that a dialkali or dialkaline salt of the precursor aromatic acid may be formed. Examples of such disalts would include 2-hydroxybenzenesulfonic acid disodium salt, 3-hydroxybenzoic acid dipotassium salt, 4-hydroxybenzenephosphonic acid dirubidium salt, etc. It is to be understood that the aforementioned hydroxylated aromatic compounds are only representative of the class of compounds which may be prepared, and that the process of the present invention as described herein is not necessarily limited thereto.

The following examples are given to illustrate the process of the present invention which, however, are not intended to limit the generally broad scope of the present invention in strict accordance therewith.

EXAMPLE I

In this example 164.0 grams (1.0 moles) of sodium benzenesulfonate and the alkali metal salt of benzenesulfonic acid, are placed in a stainless steel turbomixer autoclave containing 71.0 grams of butyronitrile and 400.0 grams of water containing 60.0 grams (1.5 moles) of sodium hydroxide. Thereafter, 18.8 grams (0.5 mole) of a 90% aqueous hydrogen peroxide solution are added to the autoclave during a period of time comprising 50 minutes. During this time, the autoclave is maintained at a temperature of 50° C. and a pressure of 5 atmospheres afforded by the introduction of substantially inert nitrogen gas. At the end of the 50 minutes, the heat is terminated and the autoclave is vented thereby allowing it to return to ambient pressure and room temperature. The treatment product is transferred to a clean, dry beaker, neutralized with sulfuric acid and extracted by an ether wash. The ether is removed from the treatment product by evaporation on a steam bath, thereby producing a crude reaction product. The treatment product is subjected to analysis by means of nuclear magnetic resonance spectroscopy instrumentation, said analysis disclosing the product to contain 2-hydroxybenzenesulfonic acid, 3-hydroxybenzenesulfonic acid and 4-hydroxybenzenesulfonic acid.

EXAMPLE II

In this example 158.0 grams (1.0 mole) of benzenephosphonic acid are placed in a stainless steel autoclave containing 19.0 grams of propionitrile dissolved in water containing 116.0 grams (2.0 moles) of potassium hydroxide. Thereafter, 30.0 grams of 50% aqueous hydrogen peroxide is added to the autoclave during a period of time comprising 60 minutes. The autoclave is maintained at a temperature of 0° C. by means of an ice bath and a pressure of 10 atmospheres afforded by the introduction of substantially inert nitrogen gas. At the end of the 60 minutes, the ice bath is removed and the autoclave is vented thereby allowing it to return to ambient pressure and room temperature. The treatment product is transferred to a beaker, neutralized, and extracted by an ether wash. The ether is removed from the treatment product by evaporation, thereby producing a crude product. The product is subjected to analysis by means of nuclear magnetic spectroscopy instrumentation, said analysis disclosing the product to contain 2-hydroxybenzenephosphonic acid.

EXAMPLE III

To a stainless steel autoclave containing 20.0 grams of acetonitrile is charged 122.0 grams (1.0 mole) of benzoic acid and 500 grams of water containing 200 grams (5.0 mole) of sodium hydroxide. Following this, 12.0 grams of a 30% aqueous hydrogen peroxide solution is added to the autoclave during a period of 20 minutes. During the addition of the aqueous hydrogen peroxide solution, the autoclave is maintained at a temperature of 50° C. and atmospheric pressure. At the end of the addition time, heating is discontinued, the autoclave is allowed to return to room temperature and the reaction product is transferred to a clean dry beaker. The product is acidified, extracted with ether and the ether layer is evaporated to produce a crude product. Fractional crystallization of the crude product in water and alcohol will yield essentially pure 2-hydroxybenzoic acid, 3-hydroxybenzoic acid and 4-hydroxybenzoic acid.

EXAMPLE IV

In a manner similar to that set forth in the above examples, 157.0 grams (1.0 mole) of 2-chlorobenzoic acid are charged to a stainless steel autoclave containing 19.0 grams of propionitrile dissolved in an aqueous sodium hydroxide solution. Following this, 20.0 grams of hydrogen peroxide is added to the autoclave during a period of time comprising 1.5 hours. The autoclave is then heated to a temperature of 100° C. and a pressure of 25 atmospheres which is afforded by the introduction of nitrogen to the autoclave. At the end of an additional 1.5 hours of time, heating is discontinued and after the autoclave has returned to room temperature, the excess pressure is discharged. The autoclave is opened and the reaction product is transferred to a flask for neutralization. The acidified mixture resulting from the neutralization is extracted by an ether wash and the ether is evaporated. The product which remains is subjected to analysis by means of nuclear magnetic resonance spectroscopy instrumentation, said analysis disclosing the product to comprise a mixture of polyhydroxy-substituted isomers of 2-chlorobenzoic acid.

EXAMPLE V

In this example 1 mole of 4-aminobenzenesulfonic acid is charged to a stainless steel autoclave containing 25 grams of butyronitrile, 500 grams of water and 48 grams of lithium hydroxide. Following this, 20.0 grams of a 30% aqueous hydrogen peroxide solution is added to the autoclave during a period of 1 hour. At the end of this time, the autoclave is sealed and nitrogen is pressed in until an initial operating pressure of 30 atmospheres is reached. The autoclave is then heated to a temperature of 75° C. and maintained thereat for an additional period of 1 hour. At the end of the 1-hour period, heating is discontinued and the autoclave is allowed to return to room temperature. After returning to room temperature, the excess pressure is discharged, the autoclave is opened and the reaction product is recovered. After neutralization of the product, it is extracted with an ether wash, the ether is evaporated and the product is subjected to analysis by means of nuclear magnetic resonance spectroscopy instrumentation, said analysis disclosing the product to comprise a mixture of hydroxy-substituted isomers of 4-aminobenzenesulfonic acid.

I claim as my invention:

1. A process for the nuclear hydroxylation of an aromatic compound having the formula:

$$R_m ArX_n H$$

in which Ar is a monocyclic or polycyclic hydrocarbon nucleus, R is selected from the group consisting of carboxylic, sulfonic, phosphonic acid groups, alkali metal or alkaline earth metal salts of the acids, X is independently selected from the group consisting of hydrogen, alkyl, aryl, cycloalkyl, alkoxy, aralkyl, alkaryl, halogen, hydroxy and amino substituents, $m$ is an integer of from 1 to about 5 and $n$ is an integer of from 0 to 5, which comprises reacting said aromatic compound with hydrogen peroxide at a temperature in the ranger of from about −10°C to about 150° C., a pressure in the range of from about atmospheric to about 100 atmospheres and a mole ratio of from about 1:1 to about 1:10 moles of hydrogen peroxide per mole of aromatic compound in the presence of a catalyst comprising an alkaline solution containing an aliphatic nitrile compound, and recovering the resultant hydroxylated aromatic compound.

2. The process as set forth in claim 1 in which said alkaline solution comprises aqueous sodium hydroxide.

3. The process as set forth in claim 1 in which said aliphatic nitrile compound is propionitrile.

4. The process as set forth in claim 1 in which said aliphatic nitrile compound is butyronitrile.

5. The process as set forth in claim 1 in which said aromatic compound is benzoic acid and said hydroxylated aromatic compound is 2-hydroxybenzoic acid.

6. The process as set forth in claim 1 in which said aromatic compound is sodium benzenesulfonate and said hydroxylated aromatic compound is 2-hydroxybenzenesulfonic acid disodium salt.

7. The process as set forth in claim 1 in which said aromatic compound is benzenephosphonic acid and said hydroxylated aromatic compound is 2-hydroxybenzenephosphonic acid.

8. The process as set forth in claim 1 in which said aromatic compound is 2-chlorobenzoic acid and said hydroxylated aromatic compound is a mixture of polyhydroxy-substituted isomers of 2-chlorobenzoic acid.

9. The process as set forth in claim 1 in which said aromatic compound is 4-aminobenzenesulfonic acid and said hydroxylated aromatic compound is a mixture of hydroxy-substituted isomers of 4-aminobenzenesulfonic acid.

* * * * *